United States Patent [19]

Purdy et al.

[11] Patent Number: 4,982,019

[45] Date of Patent: Jan. 1, 1991

[54] VOLATILE DIVALENT METAL ALKOXIDES

[75] Inventors: Andrew Purdy, Alexandria; Alan D. Berry, Springfield, both of Va.

[73] Assignee: The United States of America as represented by the Secretary of the Navy, Washington, D.C.

[21] Appl. No.: 387,048

[22] Filed: Jul. 31, 1989

[51] Int. Cl.$^5$ .............................................. C07C 31/30
[52] U.S. Cl. ................... 568/842; 568/851; 505/734
[58] Field of Search ................ 568/842, 851; 505/734

[56] References Cited

U.S. PATENT DOCUMENTS 4,260,712  4/1981  Aggarwal et al. ................... 568/851
4,717,584  1/1988  Aoki ..................................... 427/38

OTHER PUBLICATIONS

Brubaker et al., J. Inorganic Nucl. Chem., vol. 27, pp. 59–62 (1965), Pergamon Press, Northern Ireland.
Singh et al., J. Inorg. Hg. Chem., vol. 477, pp. 235–240 (1981).
Adams et al., The Aust. J. Chem., vol. 19, pp. 207–210 (1966).
Dubey et al., J. Inorganometallic, vol. 341, pp. 569–574 (1988).
Golvil et al., J. Itac. Inorg. Metal–Org. Chem., vol. 5, pp. 267–277 (1975).
Jeffries et al., Chemistry of Materials, vol. 1, pp. 8–10 (1989).
Yamane et al., Chemistry Letters (Japan), pp. 1515–1516 (1988).
Yamane et al., Chemistry Letters (Japan), pp. 939–940 (1988).
Berry et al, Formulation of High Tc Superconducting Films by Organometallic Chemical Vapor Deposition, "High-Temperature Super-Conductors II", Apr. 5–9, 1988, Reno, Nev., pp. 141–143.

*Primary Examiner*—Howard T. Mars
*Attorney, Agent, or Firm*—Thomas E. McDonnell; Barry A. Edelberg

[57] ABSTRACT

The invention relates to precursors useful for the preparation by CVD of superconducting thin films. The precursors are the volatile alkoxides of the formula $M(OR)_2$, wherein M is selected from the group consisting of Ba, Ca, and Sr, and R is selected from the group consisting of unsubstituted alkyl groups of 6 to 13 carbons and halogen substituted alkyl groups of 3 to 4 carbons wherein the halogen is selected from the group consisting of fluoride and chlorine and at least two of the halogen substitutions are fluorine. The secondary or tertiary alkyl groups are preferred and the tertiary alkyl groups are most preferred.

5 Claims, 2 Drawing Sheets

VOLATILE DIVALENT METAL ALKOXIDES

BACKGROUND OF THE INVENTION

1. Field of the Invention

This invention relates to volatile divalent metal alkoxides useful for the CVD deposition of metal oxides to a substrate. More particularly, this invention relates to volatile alkoxides of barium, strontium, or calcium used to deposit oxides used to make thin, superconducting copper oxide films.

2. Description of the Prior Art

The utility of copper oxides of barium, strontium, or calcium are well known. Difficulty exists in preparing uniform, consistent, thin films of these superconducting materials. By uniform is meant both uniform in thickness of the layer of material deposited and uniform in the chemical makeup of the layer deposited. By consistent is meant that the uniformity of the film is consistent for each run or application of a coating layer.

Chemical vapor deposition (CVD) is a well known method used in the optical fiber and semiconductor field for depositing uniform and consistent films of material. A CVD process requires volatile precursors for the oxides of the thin film. This has been a problem in making superconducting films of superconducting materials containing barium, strontium, or calcium because few volatile precursors of these oxides are known or suggested for this purpose.

Bunker et al., in U.S. Pat. No. 4,839,339, describes a precipitation method of making superconductor precursor mixtures. In the description of the state of the art, Bunker et al. notes that many methods of preparing superconductor mixed-oxides have been tried including CVD. Bunker avoids CVD and describes another process.

Metal Alkoxides of the superconducting elements have been used to make superconductors, particularly the copper oxides including $Y_1Ba_2Cu_3O_7$. The metal alkoxides are used in a solution or in gel form as described by Frahrenholtz et al., *Preparation of $YBa_2Cu_3O_{7-\delta}$ from Homogeneous Metal Alkoxide Solution*, pp. 141–147; and Laine et al., *Organometallic Precursors for the Fabrication of Hioh $T_c$ Superconducting Fibers*, pp. 450–455, both published in *Research Update*, 1988, CERAMIC SUPERCONDUCTORS II, Edited by Man F. Yan, American Ceramics Society, Inc, Westervill, Ohio; G. Moore et al., *Sol-Gel Processing of $Y_1Ba_2Cu_3O_{7-x}$ Using Alkoxide Precursors: Two Systems Yielding High Degree of Thin Film Orientation and Crystal Growth*, MATERIALS LETTERS, Vol 7, No. 12, pp. 415–424, March 1989; Horowitz et al, *Submicrometer Superconducting $YBa_2Cu_3O_{6+x}$ Particles Made by a Low-Temperature Synthetic Route*, SCIENCE, Vol. 243, pp. 66–69, Jan. 6, 1989, to prepare the copper oxide of the superconducting composition. At page 141, Fahrenholtz noted the problems with preparing superconductor thin films of the copper oxides.

Berry et al. reported making superconductor films by CVD. See Berry, A. D.; Gaskill, D. K.; Holm, R. T.; Cukauskas, E. J.; Kaplan, R.; Henry, R. L. Appl. Phys. Lett. 52(20), pp. 1743 (1988). Yamane et al. have also reported the preparation of $YBa_2Cu_3O_{7-x}$ films by CVD. The volatile precursor are metal chelates. See Yamane et al., *Preparation of $YBa_2Cu_3O_{7-x}$ Films by Chemical Vapor Deposition*, CHEMISTRY LETTERS, pp. 939–940, 1988. Yamane et al. also reports the preparation of BiSrCaCuO films by CVD. See Yamane at al., *Preparation of Bi—Sr—Ca—Cu—O Films by Chemical Vapor Deposition with Metal chelate and Alkoxide*, CHEMISTRY LETTERS, PP. 1515–1516, 1988. Shinohara et al. has reported the CVD of superconducting Y-Ba-Cu-O using a fluorine containing precursors. Initially, fluoride films are deposited and subsequently converted to the oxide with water vapor. See Shinohara, K.; Munahata, F.; Yamanaha, M., *Japn. J. Appl. Phys.* 27(9), L1683, (1988).

Studies have been made of the alkoxides, but there is a tendency for the compounds to be involatile and insoluble as reported by Adams et al., *Magnetism, Electronic Spectra, and Structure of Transition Metal Alkoxides*, Aust. J. Chem, Vol 19, pp. 207–10, 1966. Volatile Cu I alkoxides are known. Cuprous tert-Butoxide. *J. Am. Chem. Soc.*, Vol. 94:2, pp. 658–659, Jan. 26, 1972. Some volatile double ethoxides are known. Govil et al., *Some Double Ethoxides of Alkaline Earth Metals With Aluminum*, SYN. REACT. INORG. METAL-ORG. CHEM., Vol. 5(4), pp. 267–277 (1975).

In U.S. Pat. No. 4,717,584, Aoki et al. reports the preparation of magnetic thin films by plasma CVD using metal alkoxides including diethoxy, dipropoxy and dibutoxy barium and strontium. In the Aoki process, argon is bubbled through an alcohol solution of the alkoxides. The stream of argon, presumably saturated with alkoxide and alcohol, is conducted to a substrate where the alkoxide is deposited. A plasma is used to decompose the alkoxides to magnetic oxides.

As reported in the text *METAL ALKOXIDES*, Bradley et al., Academic Press New York, 1978, at pages 46–50, the alkoxides of most metals and the alkali metals and the Group II metals, such as Ba in particular, are not volatile or are sparingly volatile. Often, these alkoxides decompose instead of subliming. Some of the alkoxides are volatile such as $NaOBu^t$, Na and K fluorinated alkoxides, but writers in the field expected the stability of the alkoxides to decrease as the atomic weight of the metal atom increases. See Dear et al., *VOLATILE FLUORINATED ALKOXIDES OF THE ALKALI METALS*, Inorganic Chemistry, Vol 9, pp. 2590–2591, (1970) at p. 2591. A problem exists in providing a volatile precursor for barium, calcium and strontium which provides uniform, consistent films of superconducting films on substrates.

SUMMARY OF THE INVENTION

Accordingly, it is an object of this invention to have volatile compounds of Ba, Ca, Sr, and Cu suitable for use in the CVD preparation of superconducting films.

Further, it is an object of this invention to have compounds with sufficient volatility to be transported under vacuum or low pressure to the decomposition site in a CVD process.

In addition, it is an object of this invention to have a compound with sufficient thermal stability for the precursor molecules to arrive at the decomposition site intact.

Yet another object of this invention is to have compounds which cleanly, reproducibly and homogeneously decompose to the desired oxide in the proper elemental ratios.

Another object of this invention is to have compounds which can be transported to the deposition site without introducing undesirable elements which could contaminate the oxide film.

These and additional objects of the invention are accomplished by volatile alkoxides of Ba, Sr, and Ca. More particularly by alkoxides having between 6 and 13 carbons in the unsubstituted alkyl group, perfluorinated alkoxides containing at least 3 carbons in the fluorinated alkyl group. Volatile alkoxides of Y and Cu are known. These volatile alkoxides can be used in a CVD process where stoichiometric quantities of the material are sublimed, transported to a substrate and decomposed to an oxide, fluoride, or carbonate with or without the presence of oxygen. The oxides, fluorides, or carbonates are then treated in a known manner to produce the superconducting film.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

There has been considerable interest in recent years in the development of new precursors for &he chemical vapor deposition (CVD) of inorganic materials. In general, such precursors must be volatile, have sufficient stability to transport to the deposition site, and decompose cleanly giving the desired material. Excellent compounds for this purpose are the volatile alkoxides of the formula $M(OR)_2$, wherein M is selected from the group consisting of Ba, Ca, and Sr, and R is selected from the group consisting of unsubstituted alkyl groups of 6 to 13 carbons and halogen substituted alkyl groups of 3 to 4 carbons wherein the halogen is selected from the group consisting of fluorine and chlorine and at least two of the halogen substitutions are fluorine. The secondary or tertiary alkyl groups are preferred and the tertiary alkyl groups are most preferred.

The alkoxides are prepared by the standard techniques of reacting the metal or metal hydride with an appropriate alcohol according to the following reaction scheme.

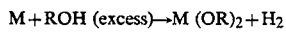

$$M + ROH \text{ (excess)} \rightarrow M(OR)_2 + H_2$$

Wherein M=Ca, Sr, Ba, and R is most preferably $CEt_3$, $CEt_2Me$, $CEt_2Pr$, $CEt_2Bu$, $CEtPrMe$, $CEtPr_2$, $CEtPrBu$, $CEtBu_2$, $CMePr_2$, $CMePrBu$, $CMeBu_2$, $CPr_3$, $CPr_2Bu$, $CPrBu_2$, $CBu_3$, $CHPr_2$, $CHPrBu$, $CHBu_2$, $C(CF_3)_3$, $CH(CF_3)_2$, $C(CF_3)_2Me$, $C(CF_2Cl)_3$, $C(CF_3)_2CCl_3$, $C(CF_2Cl)_2CCl_3$. $Me=CH_3$; $Et=CH_2Me$; $Pr=CH_2Et$ or $CHMe_2$; $Bu=CMe_3$, $CHMeEt$, or $CH_2Pr$. These alkoxides have good volatility about 250° C. and at least about a 50° C. margin to the decomposition point making these alkoxides excellent precursors for use in a CVD process where the precursor is heated to create a vapor.

Figure 1:
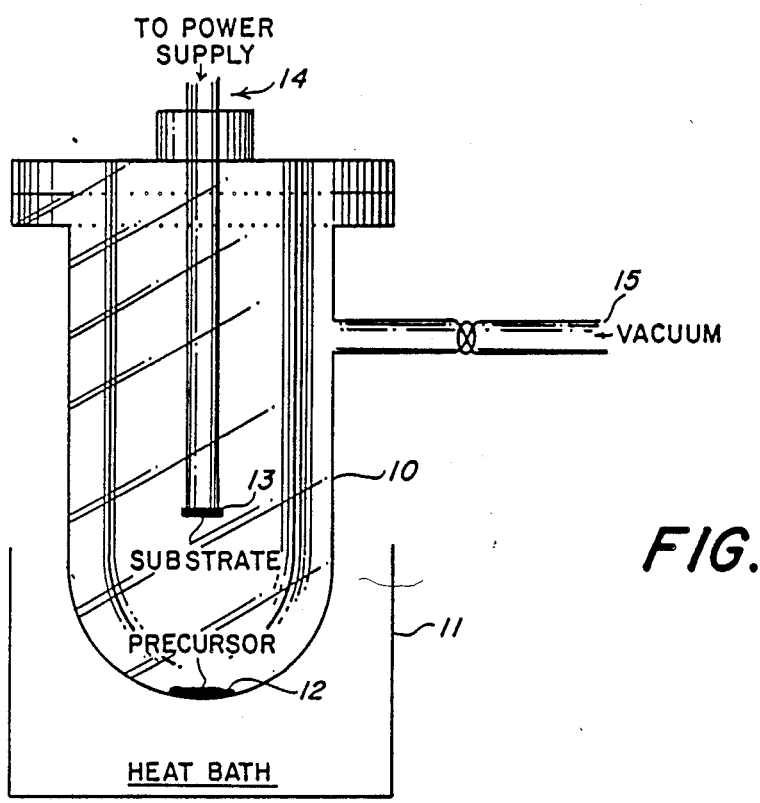
FIG. 1 is a CVD reactor for vacuum use.

In use, the alkoxides 12 of the desired superconductor are placed in the bottom of a CVD reactor 10 as shown in FIG. 1. The alkoxides are mixed in a ratio to provide the desired stoichiometric proportions of the metals. Alternatively, separate containers of each precursor can be placed in the CVD reactor. The mixed alkoxides (precursor) are heated by the bath 11 to a temperature sufficient to cause the sublimation of all the precursor materials at the desired rate. A vacuum 15 is applied. A substrate 13 is mounted above the precursor. The substrate 13 is heated by power supply 14 sufficiently to cause the precursor vapors to decompose to the oxide, fluoride or carbonate as soon as the precursors impinge upon the substrate surface. The substrate can be any substrate usually used with superconducting materials or electronic devices. These include silicon chips, quartz, $SiO_2$ chips, $GeO_2$ chips, zirconium oxide, strontium titanate, magnesium oxide etc. The end product is a substrate coated with a layer of oxide, fluoride, or carbonate materials which is subsequently treated or annealed to produce a layer of superconducting material.

Figure 2:
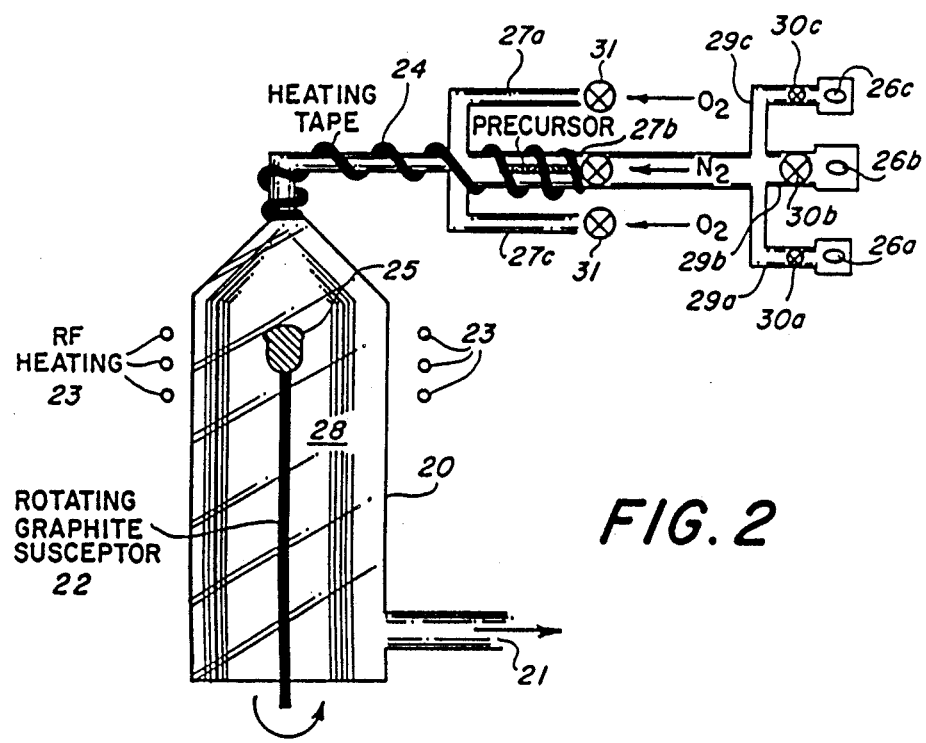
FIG. 2 is an alternate CVD reactor.

Alternatively, other CVD apparatus, such as illustrated in FIG. 2 can be used. The CVD reactor 20 is attached to a vacuum apparatus via conduit 21. The reactor 20 has a chamber 28. The chamber is heated by RF coils 23 to prevent the precipitation of the precursor or oxide on the chamber walls. A conduit 26 is connected to the chamber 28 so that oxygen and precursor may be conducted to the chamber 28. The conduit 26 is kept warm by heating tape 24 or any other heating means to avoid premature condensation of precursor. The conduit 26 is fed from the manifold 27 which contains multiple feed tubes 27 a, b etc. At least one tube carries oxygen and another carries precursor. The precursor is generated in chambers 26 a, b, etc. by heating the respective precursor above the sublimation point. A separate chamber can be used for each precursor. A neutral carrier gas can be flowed through the chambers 26 at rate sufficient to move the precursor. The stoichiometric proportions of the respective precursors can be controlled by valves 30 in manifold 29. In the alternative, a premixed combination of precursors can be placed in the manifold 27 and evaporated together. A substrate 25 is mounted on the rotating graphite susceptor 22. The precursor vapors enter the chamber 28, deposit on the substrate 25 and decompose to the oxide as a result of the energy generated by the RF heater 23. The superconductor coated substrate can be treated by known techniques in the chamber.

Group II alkoxide precursors, such as $Ba(OCEt_3)_2$, can deposit Barium oxide films under vacuum conditions, even without use of oxygen reactant. This is unlike deposition with Group II chelates, such as Ba $(TMHD)_2$ depositions which tend to require substantial oxygen flows to remove carbon. Furthermore, the volatility of the alkoxides in this invention, such as $Ba(OCEt_3)_2$, is substantially improved over previously known barium alkoxides such as $Ba(OBu^t)_2$. The latter sublimes only to a slight extent and decomposes rapidly 300°–310° C. $Ba(OCEt_3)_2$ can be heated to 350° C. before rapid decomposition takes place. Thus greater transport rates and less wastage of precursor is possible with these compounds.

Having described the invention, the following examples are given to illustrate specific applications of the invention including the best mode now known to perform the invention. These specific examples are not intended to limit the scope of the invention described in this application.

EXAMPLE 1

Reaction of Ba with Et₃COH

Et$_3$COH (5.78 g, 49.7 mmol) was condensed onto Ba (1.25 g, 9.10 mmol) in a 100 mL bulb, and stirred at 100° C. for 1 day. More Et$_3$COH (1.76 g, 15.1 mmol) was added and stirring continued another 6 days. Measurement of recovered alcohol indicates 95% completion. The white solid product is insoluble in THF, ether, and the parent alcohol.

A $\approx$1 g portion was sublimed at 290°-310° C. producing 0.33 g of white sublimate. Anal(of sublimate). Calc. (Found) for C$_{14}$H$_{30}$BaO$_2$: C, 45.73 (42.60); H, 8.22 (7.66); Ba, 37.35 (39.59). The low C, H and high Ba probably means sublimate is an oxy-alkoxide, or contains BaO. Analysis of the crude product is not reproducible since it contains particles of unreacted barium. IR (KBr, Nujol) 1155(m), 1045(w), 975(vs), 910(m), 500(w), 460(m), (C—H stretch 1 hidden by Nujol). Sublimation starts 265°-275° C., 350° C. dec.

CVD with Ba(OCEt₃)₂.

Figure 3:
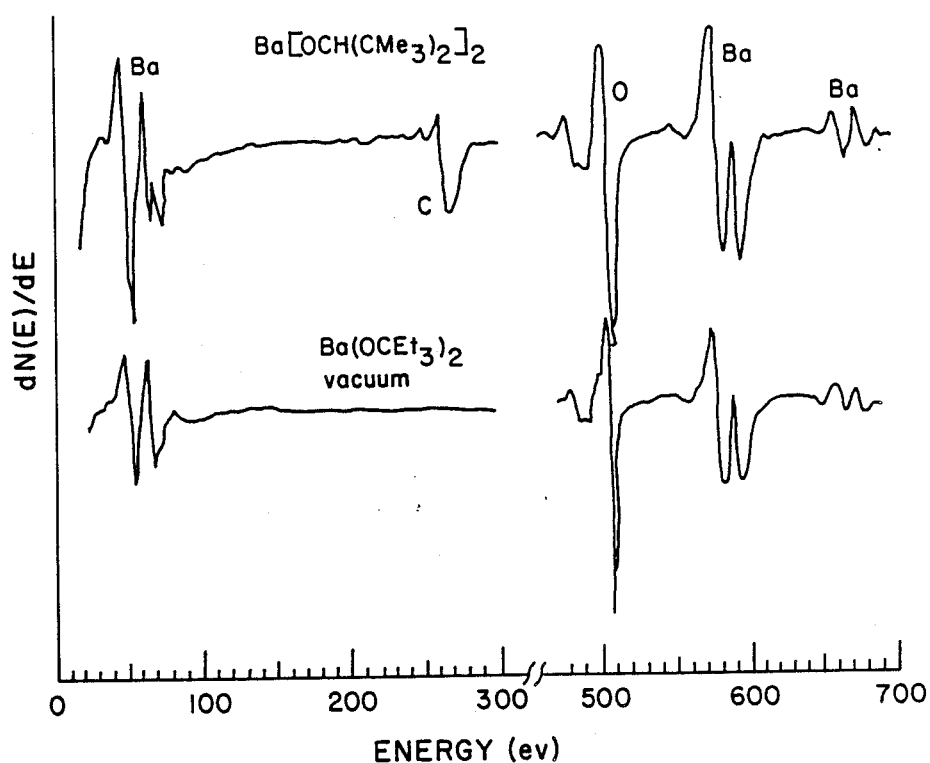
FIG. 3 is a graphic trace of the Auger spectra of thin films produced by this invention.

A vacuum CVD apparatus, as illustrated in FIG. 1, was loaded with 65 mg of Ba(OCEt3)2 (crude reaction product from above). The resistively heated Si substrate was 500°-550° C. and the air bath around the apparatus was heated until the deposition began ($\approx$250° C.). Apparently radiated heat from the substrate helps to volatilize the precursor. Deposition time was 1 hour. Auger analysis of the film (FIG. 3) showed Ba and 0 with no evidence for carbon incorporation.

EXAMPLE 2

Reaction of BaH₂ with Et₃COH

Et$_3$COH (4 mL, 28.4 mmol) was condensed onto BaH$_2$ (1.01 g, 7.75 mmol). A vigorous reaction started quickly, then subsided. Stirring at $\approx$60° C. for 12 hours liberated 3.65 mmol non-condensable gas, another day released 5.3 m, and another day 0.72 mmol. Heating up to 120° C. for several days produced no more hydrogen. An attempt was made to dissolve the product in hot NNN'N'-TMEDA which failed. The TMEDA was decanted and the white solid dried in vacuo, 1.81 g was isolated. Anal. Calc. (Found) for C$_{14}$H$_{30}$BaO$_2$ C, 45.73 (42.21); H, 8.22 (7.52); Ba, 37.35 (40.69). Analysis indicates either the presence of unreacted BaH$_2$ or an oxide-alkoxide.

EXAMPLE 3

Ba[OCH(CMe₃)₂]₂

(Me$_3$C)$_2$CHOH (1.31 g, 9.08 mmol) was condensed onto Ba (0.30 g, 2.2 mmol) in a 25 mL bulb. Gas evolution was proceeding at 80° C., but temperature accidentally reached 120° C. and a brown color formed. After stirring for 4 hours at 90°-95° C., the non-condensable gas was measured (2.2 mmol), and 0.696 g (Me$_3$C)$_2$CHOH was recovered. The product was dissolved in hot THF, filtered twice, and evaporated. A white powder (0.43 g, 46%) was obtained by dissolving the crude product in hot THF/C$_6$H$_6$ mixture and allowing to cool. Anal. Calc. (Found) for C$_{18}$H$_{38}$BaO$_2$: C, 51.0 (51.15); H, 9.0 (9.19); Ba, 32.4 (32.08). IR (KBr, Nujol) 2730(w), 2650(w), 2520(w), 2450(w), 1365(m), 1350(m), 1065(vs), 1005(s), 945(w), 920(w), 605(w), 540(w, br). NMR (1H, C$_6$D$_6$, 60 MHz) δ 0.96 (Me), CH not positively identified. Sublimation: 260°-270° C., 320° C. dec.

CVD with Ba[OCH(CMe₃)₂]₂

A vacuum CVD apparatus, such as illustrated in FIG. 1, was loaded with 70 mg precursor. Substrate (Si) was heated 550°-600° C. and deposition began with air bath 240°-250° C. Deposition time 1 hour. Auger analysis (FIG. 3) indicates Ba, O, and substantial carbon incorporation.

EXAMPLE 4

Ca[OC(CF₃)₃]₂ (Ca[PFTB]₂)

(CF$_3$)$_3$OH (2.11 g, 8.94 mmol) was condensed onto Ca (0.08 g, 2.0 mmol) and undergoes a very slow reaction at room temperature. Mixture was stirred for 12 h at 95° C. and 7 days at 120°-130° C. Hydrogen measurement (0.00054 mol) indicates 27% completion. THF was added to dissolve coating on Ca and heated 7 more days, at which time hydrogen measurement indicates 66% completion. After removal of volatiles, the product was dissolved in ether, filtered, dried, and recrystallized from THF/heptane to yield 0.50 g of a yellow-white powder. Anal. Calc. (Found) for C$_8$F$_{18}$CaO$_2$ C, 18.8 (20.91); H, 0 (1.25); F, 67.0 (59.74); Ca 7.9 (6.79). Material apparently contains solvent which is removable at 130° C. under vacuum. After 0.103 g was used for a CVD experiment, sublimation (140°-190° C.) of the remainder resulted in 0.22 g of white powder.

CVD with Ca[OC(CF₃)₃]₂

Vacuum CVD apparatus was loaded with 103 mg of crude Ca(PFTB)$_2$ With substrate at 600°-650° C., deposition began when air bath reached 165° C. Temperature was allowed to rise to 205° C. over ½ hour and deposition proceeded 45 min at 205° C. Auger analysis of film indicated Ca and F, small amount of O, and no detectable Carbon.

EXAMPLE 5

Sr[PFTB]₂

(CF$_3$)$_3$COH (7 mmol) was condensed onto Sr (0.1929 g, 2.202 mmol) in a tube. Little reaction occurred at ambient temperature or when heated 65°-70° C. for ¼ hour. Reaction proceeded slowly at 80° C. and was refluxed for 4 days at 93°-94° C. until no further non-condensable gasses were produced. Removal of volatiles (0.6105 g, 2.59 mmol HPFTB) left a white solid (1.23 g, 100%) in the tube. A portion was crystallized from heptane/THF solution. Anal. Calc. (Found) for C$_8$F$_{18}$SrO$_2$: C, 17.41 (17.20); H, 0 (0); F, 61.10 (61.31); Sr, 15.66 (15.70). Sublimed 230° C.

EXAMPLE 6

Ba[PFTB]₂

(CF$_3$)$_3$COH (0.8688 g, 3.681 mmol) was condensed onto Ba (0.1073 g, 0.781 mmol), and heated to 95.C for 3 days. A total of 2.122 mmol H-PFTB was recovered when the volatiles were removed. A portion of the white solid was removed and the remainder was dissolved in THF, filtered, and dried under vacuum for 3 days at 90° C. Anal. Calc. (Found) for C$_8$F$_{18}$BaO$_2$: C, 15.82 (16.01); H, 0 (0); F, 56.3 (56.12); Ba, 22.6 (22.50). Sublimed 280° C.

Obviously, many modifications and variations of the present invention are possible in light of the above teachings. It is therefore to be understood that, within the scope of the appended claims, the invention may be practiced otherwise than as specifically described.

What is claimed is:

1. A compound of the formula M(OR)$_2$, wherein M is selected from the group consisting of Ba, Ca, and Sr, and R is selected from the group consisting of halogen substituted alkyl groups of 3 to 4 carbons wherein the halogen is selected from the group consisting of fluorine and chlorine and at least two of the halogen substitutions are fluorine.

2. A compound of the formula M(OR)$_2$ wherein M is selected from the group consisting of Ba, Ca, and Sr, and R is selected from the group consisting of C(CF$_3$)$_3$, CH(CF$_3$)$_2$, C(CF$_3$)$_2$Me, C(CF$_2$Cl)$_3$, C(CF$_3$)$_2$CCL$_3$, C(CF$_2$Cl)$_2$CCl$_3$.

3. The compound of claim 3 where in M is Ba and R is C(CF$_3$)$_3$.

4. The compound of claim 3 where in M is Ca and R is C(CF$_3$)$_3$.

5. The compound of claim 3 wherein M is Sr and R is C(CF$_3$)$_3$.